US008378135B2

(12) United States Patent
Prasad et al.

(10) Patent No.: US 8,378,135 B2
(45) Date of Patent: Feb. 19, 2013

(54) MULTIFUNCTIONAL ALCOHOLS OBTAINED FROM CARDANOL, MULTIFUNCTIONAL ACRYLIC CROSSLINKER AND PENDANT PHOSPHOROUS FLAME RETARDANT DERIVATIVES THEREOF

(75) Inventors: Vadakkethonippurathu Sivankutty Nair Prasad, Kerala (IN); Chennakkattu Krishna Sadasivan Pillai, Kerala (IN)

(73) Assignee: Council of Scientific and Industrial Research, New Delhi (IN)

(*) Notice: Subject to any disclaimer, the term of this patent is extended or adjusted under 35 U.S.C. 154(b) by 869 days.

(21) Appl. No.: 12/097,354

(22) PCT Filed: Dec. 30, 2005

(86) PCT No.: PCT/IN2005/000458
§ 371 (c)(1),
(2), (4) Date: Nov. 13, 2008

(87) PCT Pub. No.: WO2007/077567
PCT Pub. Date: Jul. 12, 2007

(65) Prior Publication Data
US 2009/0240078 A1    Sep. 24, 2009

(51) Int. Cl.
C07C 69/54 (2006.01)
C07C 67/02 (2006.01)
C07F 9/02 (2006.01)

(52) U.S. Cl. .......... 558/70; 560/221; 560/249; 560/254; 558/89; 558/99

(58) Field of Classification Search .......... None
See application file for complete search history.

(56) References Cited

U.S. PATENT DOCUMENTS

| | | | | |
|---|---|---|---|---|
| 3,057,928 A * | 10/1962 | Koblitz et al. | ................ | 568/723 |
| 4,141,871 A | 2/1979 | Shimp et al. | ................. | 260/29.4 |
| 4,751,267 A | 6/1988 | Berghoff | ...................... | 525/108 |
| 5,993,911 A | 11/1999 | Brenke et al. | .................. | 427/407 |
| 6,001,953 A | 12/1999 | Davis et al. | ................... | 528/196 |
| 6,060,539 A | 5/2000 | Hermansen et al. | .......... | 523/400 |
| 6,060,577 A | 5/2000 | Davis | ............................ | 528/196 |
| 6,133,404 A | 10/2000 | Kang et al. | ..................... | 528/179 |
| 6,211,262 B1 | 4/2001 | Mejiritski et al. | .............. | 522/71 |
| 6,229,054 B1 | 5/2001 | Dai et al. | ....................... | 568/630 |
| 6,255,439 B1 | 7/2001 | Avadhani et al. | ............. | 528/196 |
| 6,300,460 B1 | 10/2001 | McCloskey et al. | .......... | 528/196 |
| 6,441,123 B1 | 8/2002 | Hariharan et al. | ............ | 528/196 |
| 6,451,957 B1 | 9/2002 | Varma et al. | .................. | 528/196 |
| 6,525,112 B1 | 2/2003 | Bammel | ........................ | 523/404 |
| 6,537,636 B1 | 3/2003 | Wisnudel et al. | ............. | 428/641 |
| 6,548,189 B1 | 4/2003 | Gunasekaran | ................. | 428/626 |
| 6,548,623 B2 | 4/2003 | Brunelle et al. | .............. | 528/196 |
| 6,569,918 B2 | 5/2003 | Waitkus et al. | ............... | 523/145 |
| 6,569,928 B1 | 5/2003 | Levchik et al. | ............... | 524/115 |
| 6,583,258 B1 | 6/2003 | Lemmon et al. | ............. | 528/198 |
| 6,608,164 B2 | 8/2003 | Lemmon et al. | ............. | 528/196 |
| 6,723,765 B2 | 4/2004 | Bammel | ....................... | 523/415 |

OTHER PUBLICATIONS

Abraham et al., "Copolyesters of Hydroxyphenylalkanoic Acids: Synthesis and Thermal Properties of Poly((4-Oxybenzoate)-Co-(8-(3-Oxyphenyl)Octanoate))and Poly((3- Bromo-4-Oxybenzoate)-Co-(8-(3-Oxyphenyl)Octanoate))," *Polymer International*, 51(6):475-480, 2002.
Agrawal et al., "Cardanol-Based Epoxy Flexibilizers for Inhibition of Composite Propellants," *Journal of Macromolecular Science-Pure and Applied Chemistry*, A30(1):19-34, 1993.
Amorati et al., "Absolute rate constants for the reaction of peroxyl radicals with cardanol derivatives," *Journal of the Chemical Society-Perkin Transactions 2*, 11:2142-2146, 2001.
Antony and Pillai, Synthesis and Thermal Characterization of Chemically-Modified Cardanol Polymers, *Journal of Applied Polymer Science*, 49(12):2129-2135, 1993.
Antony et al., "Synthesis and Thermal Characterization of Chemically-Modified Phenolic Resins," *Journal of Applied Polymer Science*, 54(4):429-438, 1994.
Antony, "Synthesis, Characterization, and Thermal Studies of Cardanol-Based Polyphosphate Esters," *Journal of Polymer Science Part A—Polymer Chemistry*, 31(13):3187-3191, 1993.
Attanasi et al., "Novel phthalocyanines containing cardanol derivatives," *Journal of Porphyrins and Phthalocyanines*, 7(1):52-57, 2003.
Attanasi et al., "Regioselective bromination of cardanol derivatives," *Organic Preparations and Procedures International*, 27(6):645-650, 1995.
Bezerra et al., "Synthesis of Neoflavonoids-4-(4'-Methoxyphenyl)3,4-Dihydrocoumarins," *Journal of the Brazilian Chemical Society*, 8(3):229-234, 1997.
Bhunia et al., "Synthesis and Characterization of Polymers from Cashewnut Shell Liquid, a Renewable Resource III—Synthesis of a Polyether," *European Polymer Journal*, 35(9):1713-1722, 1999.
Bhunia et al., "Synthesis and Characterization of Polymers from Cashewnut Shell Liquid, a Renewable Resource II—Synthesis of Polyurethanes," *European Polymer Journal*, 35(8):1381-1391, 1999.
Bhunia et al., "Synthesis and Characterization of Polymers from Cashewnut Shell Liquid—A Renewable Resource V—Synthesis of Copolyester," *European Polymer Journal*, 36(6):1157-1165, 2000.

(Continued)

*Primary Examiner* — Paul A Zucker
(74) *Attorney, Agent, or Firm* — Fulbright & Jaworski L.L.P.

(57) ABSTRACT

Multifunctional alcohols, polyols derived from cardanol containing at least 3 hydroxyl groups are disclosed. Such alcohols allow for synthesis of multifunctional crosslinkers such as acrylates, epoxies, and vinyl ethers and flame retardants such as >phosphates. The multifunctional alcohols or polyols can be used in polyurethanes and polycarbonates. The multifunctional crosslinkers can be used in optical coating and waveguide compositions to increase curing speed and crosslink density. The multifunctional phosphates can be used in flame resistant plastics as the highly pendant phosphorus containing phosphate non-halogen flame retardant additives.

13 Claims, No Drawings

OTHER PUBLICATIONS

Bhunia et al., "Synthesis of Polyurethane from Cashew Nut Shell Liquid, a Renewable Resource," *Journal of Polymer Science Part A—polymer Chemistry*, 36(3):391-400, 1998.

Bolton et al., "Biologically-Active Derivatives of Cardanol—Antifungal 8-Aryloctanoic Acids," *Natural Product Letters*, 4(3):227-233, 1994.

Das et al., "Polymers from Renewable Resources—XXVIII—Synthesis, Characterization, and Thermal Studies of Semiinterpenetrating Polymer Networks Derived from Castor-Oil-Based Polyurethanes and Cardanol Derivatives," *Polymer-Plastics Technology and Engineering*, 37(4):427-435, 1998.

De Avellar et al., "New Quaternary Ammonium-Salts Derived from Cardanol and Their Use as Phase-Transfer Catalyst," *Journal of the Brazilian Chemical Society*, 11(1):22-26, 2000.

Graham et al., "Ozonization of Phenols from Anacardium-Occidentale (Cashew)," *Journal of the American Oil Chemists Society*, 79(7):725-732, 2002.

Guru et al., "Polymers from Renewable Resources—Xxvii—Studies on Synthesis, Characterization, and Thermal-Properties of Resins Derived from Cardanyl Acrylate- Furfural-Organic Compounds," *Polymer-Plastics Technology and Engineering*, 38(1):179-187, 1999.

Huong et al., "Cardanol-Phenol-Formaldehyde Resins—Thermal-Analysis and Characterization," *Angewandte Makromolekulare Chemie*, 243(DEC):77-85, 1996.

Ikeda et al., "A New Cross-Linkable Polyphenol from a Renewable Resource," *Macromolecular Rapid Communications*, 21(8):496-499, 2000.

Ikeda et al., "Enzymatic-Synthesis and Curing of Poly(Cardanol)," *Polymer Journal*, 32(7):589-593, 2000.

Ikeda et al., "Man-Made Urushi—Preparation of Cross-Linked Polymeric Films from Renewable Resources via Air-Oxidation Processes," *Proceedings of the Japan Academy Series B-Physical and Biological Sciences*, 76(10):155-160, 2000.

Ikeda et al., "Synthesis and Curing Behaviors of a Cross-Linkable Polymer from Cashew Nut Shell Liquid," *Polymer*, 43(12):3475-3481, 2002.

International Preliminary Report on Patentability issued in International Application No. PCT/IN2005/000458, mailed Jul. 10, 2008.

International Search Report issued in International Application No. PCT/IN2005/000458, mailed Jun. 8, 2006.

John et al., "Self-cross-linkable monomer from cardanol—cross-linked beads of poly(cardanyl acrylate) by suspension polymerization," *Makromolekulare Chemie-Rapid Communications*, 13(5):255-259, 1992.

John et al., "Synthesis and Characterization of a Self-Cross-Linkable Polymer from Cardanol—Autooxidation of Poly(Cardanyl Acrylate) to Cross-Linked Film," *Journal of Polymer Science Part A—Polymer Chemistry*, 31(4):1069-1073, 1993.

Kobayashi et al., "Artificial Urushi," *Chemistry—A European Journal*, 7(22):4755-4760, 2001.

Lee et al., "Phospholipase C-Gamma-1 Inhibitory Principles from the Sarcotestas of Ginkgo-Biloba," *Journal of Natural Products*, 61(7):867-871, 1998.

Lin et al., "Study on the Cardanol-Aldehyde Condensation Polymer Containing Boron-Nitrogen Coordinate Bond," *Chinese Journal of Polymer Science*, 16(3):219-225, 1998.

Lubi et al., "Cashew Nut Shell Liquid—A Versatile Monomer for Polymer Synthesis," *Designed Monomers and Polymers*, 3(2):123-153, 2000.

Manjula et al., "Kinetics and Mechanism of Oligomerization of Cardanol Using Acid Catalysts," *Journal of Applied Polymer Science*, 45(2):309-315, 1992.

Menon et al., "Chemical Cross-Link Density and Network Structure of Natural-Rubber Vulcanizates Modified with Phosphorylated Cardanol Prepolymer," *Journal of Applied Polymer Science*, 51(13):2157-2164, 1994.

Mhaske et al., "Synthesis and Characterization of End-Capped Polyimides and Their Gas-Permeability Properties;" *Journal of Applied Polymer Science*, 77(3):627-635, 2000.

Mishra et al., "Polymers from Renewable Resources .10. Semiinterpenetrating Polymer Networks Based on Castor-Oil Polyurethane and Cardanol-Furfural Resin—Scanning Electron-Microscopy and XRD Studies," *Journal of Macromolecular Science-Pure and Applied Chemistry*, A32(S4):499-510, 1995.

Mishra et al., "Polymers from Renewable Resources .7. Thermal-Properties of the Semiinterpenetrating Polymer Networks Composed of Castor-Oil Polyurethanes and Cardanol-Furfural Resin," *Polymer Engineering and Science*, 36(8):1047-1051, 1996.

Mohapatra et al., "Polymers from Renewable Resources-21 Semiinterpenetrating Polymer Networks Based on Cardanol-Formaldehyde-Substituted Aromatic-Compounds Copolymerized Resins and Castor-Oil Polyurethanes—Synthesis, Structure, Scanning Electron-Microscopy and XRD," *Journal of Polymer Science Part A—Polymer Chemistry*, 35(15):3117-3124, 1997.

Moreira et al., "Stabilization of Asphaltenes by Phenolic-Compounds Extracted from Cashew-Nut Shell Liquid," *Journal of Applied Polymer Science*, 73(1):29-34, 1999.

Nair et al., "Cyanate Esters Based on Cardanol Modified-Phenol-Formaldehyde Resins—Syntheses and Thermal-Characteristics," *Journal of Polymer Science Part α-Polymer Chemistry*, 33(4)621-627, 1995.

Nair et al., "Recent Advances in Phenolic Resins," *Metals Materials and Processes*, 9(2):179-200, 1997.

Nayak et al., "Polymers from Renewable Resources .11. Synthesis and Characterization of Thermosetting Resins Derived from Cardanyl Acrylate Formaldehyde-Substituted Aromatic-Compounds," *Journal of Macromolecular Science-Pure and Applied Chemistry*, A32(S4):511-521, 1995.

Nguyen et al., "Cure Kinetics of the Cardanyl Acrylate-Styrene System Using Isothermal Differential Scanning Calorimetry," *Journal of Applied Polymer Science*, 85(9):2034-2039, 2002.

Paul et al., "Melt/Solution Processable Conducting Polyaniline with Novel Sulfonic-Acid Dopants and Its Thermoplastic Blends," *Synthetic Metals*, 114(1):27-35, 2000.

Pillai et al., "A Comparative-Evaluation of a Novel Flame-Retardant, 3-(Tetrabromopentadecy1)-2,4,6-Tribromophenol (TBPTP) with Decabromodiphenyloxide (DBDPO) for Applications in LDPE-Based and EVA-Based Cable Materials," *Journal of Applied Polymer Science*, 66(11):2157-2173, 1997.

Pillai et al., "Thermotropic Liquid-Crystalline Copolyester Based on 8-(3-Hydroxyphenyl) Octanoic-Acid and Para-Hydroxybenzoic Acid," *Polymer*, 33(18):3968-3970, 1992.

Pillai, "Liquid-Crystalline Polymers—The Effects of Chain Disrupters," *Pure and Applied Chemistry*, 70(6):1249-1252, 1998.

Pillot et al., "The Use of Naturally-Occurring Phenols in the Synthesis of Novel Functional Polysiloxanes," *Surface Coatings International Part B-Coatings Transactions*, 84(3):197-204, 2001.

Prasad et al., "Flame Retardation of Polyethylene—Effect of a Phosphorus Flame-Retardant Having Both Hydrophobic and Hydrophilic Groups in the Same Molecule," *Journal of Applied Polymer Science*, 77(12):2631-2640, 2000.

Roth et al., "Dioxygenation of Long-Chain Alkadien(Trien)ylphenols by Soybean Lipoxygenase," *Journal of Agricultural and Food Chemistry*, 46(8):2951-2956, 1998.

Sahoo et al., "Polymers from Renewable Resources-6: Synthesis and Characterization of Thermosetting Resins Derived from Cashewnut Shell Liquid Formaldehyde Substituted Aromatic-Compounds," *Angewandte Makromolekulare Chemie*, 233(NOV):1-13, 1995.

Saladino et al., "A new and efficient synthesis of ortho-benzoquinones and para-benzoquinones of cardanol derivates by the catalytic-system methyl rhenium trioxide (MTO)/$H_2O_2$," *Journal of the Chemical Society-Perkin Transactions 1*, 4:581-586, 2000.

Saladino et al., "Microencapsulated methyl rhenium trioxide (MTO)/$H_2O_2$ systems for the oxidation of cardanol derivatives," *Pure and Applied Chemistry*, 75(2-3):265-272, 2003.

Saladino et al., "Selective oxidation of phenol and anisole derivatives to quinones with hydrogen-peroxide and polymer-supported methylrhenium trioxide systems," *Tetrahedron*, 58(42):8493-8500, 2002.

Saminathan et al., "Synthesis and Characterization of Main-Chain Liquid-Crystalline Polymers Containing a P-Phenyleneazo Group," *Macromolecules*, 26(25):7103-7105, 1993.

Saminathan et al., "Synthesis of Novel Liquid-Crystalline Polymers with Cross-Linked Network Structures," *Polymer*, 41(8):3103-3108, 2000.

Shobha et al., "Inhibition of Soybean Lipoxygenase-1 by Anacardic Acids, Cardols and Cardanols," *Journal of Natural Products*, 57(12):1755-1757, 1994.

Shobha et al., "Phenolic Lipid-Composition During Development of Cashew," *Phytochemistry*, 31(7):2295-2297, 1992.

Short et al., "Long-chain phenols-30. A rate study of the mannich reaction of phenols (with particular reference to 3-pentadecylphenol)," *Journal of Chemical Technology and Biotechnology*, 53(4):389-396, 1992.

Sreelatha et al., "Isopropyl-3-pentadecylphenyl phosphoric-acid—A new reagent for liquid-liquid-extraction and separation of rare-earths," *Analytical Letters*, 26(3):573-591, 1993.

Swain et al., "Polymer from Renewable Resources—Studies on Synthesis, Characterization, and Thermal-Properties of Resins Derived from Diazotized Cardanol-Formaldehyde-Organic Compounds," *Polymer-Plastics Technology and Engineering*, 39(5):927-936, 2000.

Swain et al., "Polymers from Renewable Resources-5. Synthesis and Characterization of Thermosetting Resins Derived from Cashew Nut Shell Liquid (CNSL)-Furfural-Substituted Aromatic-Compounds," *Journal of Applied Polymer Science*, 54(10):1413-1421, 1994.

Tagliatesta et al., "Manganese and iron tetraphenylporphyrin-catalyzed oxidation of a cardanol derivative (Hydrogenated tert-butylcardanol)," *Journal of Porphyrins and Phthalocyanines*, 6(1):12-16, 2002.

Tan, "Cardanol-Glycols and Cardanol-Glycol-Based Polyurethane Films," *Journal of Applied Polymer Science*, 65(3):507-510, 1997.

Tan, "Cardanol-Lignin-Based Epoxy-Resins—Synthesis and Characterization," *Journal of Polymer Materials*, 13(3):195-199, 1996.

Tan, "Cardanol-Lignin-Based Polyurethanes," *Polymer International*, 41(1):13-16, 1996.

Tan, "Thermoplastic Composites Based on Jute Fiber Treated with Cardanol-Formaldehyde," *Polymers & Polymer Composites*, 5(45):273-279, 1997.

Thien et al., "Modification of rubber by cardanol-formaldehyde resins and epoxidized cardanol," *Journal of Macromolecular Science—Pure and Applied Chemistry*, A33(12):1963-1972, 1996.

Tyman et al., "Synthesis and characterization of polyethoxylate surfactants derived from phenolic lipids," *Journal of Surfactants and Detergents*, 6(4):291-297, 2003.

Uyama and Kobayashi, "Enzymatic Polymerization Yields Useful Polyphenols," *Chemtech*, 29(10):22-28, 1999.

Zhang and Horrocks, "A review of flame retardant polypropylene fibres," *Prog. Polym. Sci.* 28(11):1517-1538, 2003.

* cited by examiner

US 8,378,135 B2

MULTIFUNCTIONAL ALCOHOLS OBTAINED FROM CARDANOL, MULTIFUNCTIONAL ACRYLIC CROSSLINKER AND PENDANT PHOSPHOROUS FLAME RETARDANT DERIVATIVES THEREOF

This Application is a National Phase Application of International Application No. PCT/IN2005/000458 filed Dec. 30, 2005.

FIELD OF THE INVENTION

The invention is directed to a class of multifunctional long chain alcohols or polyols containing substituted or unsubstituted aryl unit derived from cardanol which is a byproduct of cashew nut processing industry and their derivatives such as acrylates and methacrylates collectively referred to herein as acrylates, and phosphates and polyphosphates collectively referred to herein as phosphates, epoxies and vinyl ethers. The acrylates, epoxies and vinyl ethers are used as crosslinkers in compositions for optical coatings and waveguide devices. Prior art references have disclosed that multifunctional acrylate polymers may be used for coating applications.

BACKGROUND OF THE INVENTION

Cardanol is a meta-alkene substituted aromatic phenol extracted from cashew nut shell liquid hereinafter referred as CNSL exudates of *Anacardium occidentale* L and a byproduct of cashew processing industry. A number of published literatures are on the derivatisation and use of cardanol in polymerization and in polyurethanes and epoxies.

Modifications of cardanol and its uses have been widely reported. See, for example, the U.S. Pat. No. 6,723,765 Autodeposited coating of epoxy and OH groups-containing resin with NCO lower T-crosslinker and higher T-crosslinker; U.S. Pat. No. 6,608,164 Salts of heterocyclic diols as catalysts for melt polycarbonate, U.S. Pat. No. 6,583,258 Salts of organic phosphates as catalysts for melt polycarbonate; U.S. Pat. No. 6,569,928 Phosphorus-containing fire retardant thermoplastic polyester composition; U.S. Pat. No. 6,569,918 Polymer composition for curing novolac resins; U.S. Pat. No. 6,548,623 Method of polycarbonate preparation; U.S. Pat. No. 6,548,189 Epoxy adhesive; U.S. Pat. No. 6,537,636 Data storage media containing clear polycarbonate blends; U.S. Pat. No. 6,525,112 Autodepositable prepolymer of epoxy- and OH-containing resin and hybrid isocyanate crosslinker; U.S. Pat. No. 6,451,957 (Hydroxyalkyl)phenols, method for their preparation, and uses thereof; U.S. Pat. No. 6,441,123 Vibration damping monolithic polymers; U.S. Pat. No. 6,255,439 1,1-Bis(4-hydroxyphenyl)-3-alkylcyclohexanes, method for their preparation and polycarbonates prepared there from; and U.S. Pat. No. 6,229,054 Derivative of cardanol and uses therefore.

Acrylic and phosphate derivatives of cardanol were also exemplified in the following US patents or publications. U.S. Pat. No. 6,211,262 Corrosion resistant, radiation curable coating; U.S. Pat. No. 6,177,537 Polycarbonates suitable for use in optical articles; U.S. Pat. No. 6,133,404 Polyester and formation process thereof U.S. Pat. Nos. 6,060,577; 6,060,539 Room-temperature stable, one-component, thermally-conductive, flexible epoxy adhesives; U.S. Pat. No. 6,001,953 Polycarbonates suitable for use in optical articles; U.S. Pat. No. 5,993,911 Aqueous coating compositions using polyalkylene glycol dialkyl ethers and process for multi-layer lacquer coating; U.S. Pat. No. 4,751,267 Acrylic polyester high solids coatings, U.S. Pat. No. 4,141,871 Aqueous dispersions of polyhydroxy polyether resins as coating compositions for metallic substrates.

Cardanol modifications are exemplified in the following publications. JHP Tyman, I E Bruce, Synthesis and characterization of polyethoxylate surfactants derived from phenolic lipids, Journal of Surfactants and Detergents, 2003, Vol 6, Iss 4, pp 291-297; R Saladino, E Mincione, O A Attanasi, P Filippone, Microencapsulated methyl rhenium trioxide (MTO)/$H_2O_2$ systems for the oxidation of cardanol derivatives; Pure and Applied Chemistry, 2003, Vol 75, Iss 2-3, pp 265-272; Saladino-R Neri-V Mincione-E Marini-S Coletta-M Fiorucci-C Filippone-P, A New and Efficient Synthesis of Ortho-Benzoquinones and Para-Benzoquinones of Cardanol Derivatives by the Catalytic-System methyl rhenium trioxide (MTO)/$H_2O_2$, Journal of the Chemical Society-Perkin Transactions 1, 2000, Iss 4, pp 581-586; O A Attanasi, G Ciccarella, P Filippone, G Mele, J Spadavecchia, G Vasapollo, Novel Phthalocyanines containing cardanol derivatives, Journal of Porphyrins and Phthalocyanines, 2003, Vol 7, Iss 1, pp 52-57; Attanasi-O A Buratti-S Filippone-P, Regioselective Bromination of Cardanol Derivatives, Organic Preparations and Procedures International 1995, Vol 27, Iss 6, pp 645-650;

Amorati-R Pedulli-G F Valgimigli-L Attanasi-O A Filippone-P Fiorucci-C Saladino-R, Absolute Rate Constants for the Reaction of Peroxyl Radicals with Cardanol Derivatives, Journal of the Chemical Society-Perkin Transactions 2 2001, Iss 11, pp 2142-2146, Saladino-R Neri-V Mincione-E Filippone-P, Selective Oxidation of Phenol and Anisole Derivatives to Quinones with Hydrogen-Peroxide and Polymer-Supported Methylrhenium Trioxide Systems, *Tetrahedron* 2002, Vol 58, Iss 42, pp 8493-8500, Tagliatesta-P Crestini-C Saladino-R Neri-V Filippone-P Fiorucci-C Attanasi-O A, Manganese and Iron Tetraphenylporphyrin-Catalyzed Oxidation of a Cardanol Derivative (Hydrogenated tert-Butylcardanol), Journal of Porphyrins and Phthalocyanines 2002, Vol 6, Iss 1, pp 12-16.

Short-E L, Tychopoulos-V, Tyman-J H P, Long-Chain Phenols-30. A Rate Study of the Mannich Reaction of Phenols (with Particular Reference to 3-Pentadecylphenol), Journal of Chemical Technology and Biotechnology 1992, Vol 53, Iss 4, pp 389-396, John-G, Pillai-C K S, Self-Cross-Linkable Monomer from Cardanol—Cross-Linked Beads of Poly(Cardanyl Acrylate) by Suspension Polymerization, Makromolekulare Chemie-Rapid Communications 1992, Vol 13, Iss 5, pp 255-259; Sreelatha-S Rao-T P Narayanan-C S Damodaran-A D, Isopropyl-3-Pentadecylphenyl Phosphoric-Acid-A New Reagent for Liquid-Liquid-Extraction and Separation of Rare-Earths, analytical letters 1993, Vol 26, Iss 3, pp 573-591, Bezerra-M Z B Machado-M I L Demorais-S M Braz-R, Synthesis of Neoflavonoids-4-(4'-Methoxyphenyl)3,4-Dihydrocoumarins, Journal of the Brazilian Chemical Society 1997, vol 8, iss 3, pp 229-234; Roth-M Gutsche-B Herderich-M Humpf-H U Schreier-P, Dioxygenation of Long-Chain Alkadien(Trien)ylphenols by Soybean Lipoxygenase, Journal of Agricultural and Food Chemistry 1998, Vol 46, Iss 8, pp 2951-2956, Deavellar-I G J Godoy-K Demagalhaes-G C, Quaternary Ammonium-Salts Derived from Cardanol and Their Use as Phase-Transfer Catalyst, Journal of the Brazilian Chemical Society 2000, Vol 11, Iss 1, pp 22-26; Ikeda-R Tanaka-H Uyama-H Kobayashi-S A New Cross-Linkable Polyphenol from a Renewable Resource Macromolecular Rapid Communications 2000, Vol 21, Iss 8, pp 496-499; Graham-M B Tyman-J H P, Ozonization of Phenols from Anacardium-Occidentale (Cashew), Journal of the American Oil Chemists Society 2002, Vol 79, Iss 7, pp 725-732.

Investigations on Composition and bioactivity of cardanol were reported in the following examples. Phenolic Lipid-Composition During Development of Cashew, Phytochemistry 1992, Vol 31, Iss 7, pp 2295-2297; Bolton-R Demorais-S M, Biologically-Active Derivatives of Cardanol—Antifungal 8-Aryloctanoic Acids, Natural Product Letters 1994, Vol 4, Iss 3, pp 227-233; Shobha-S V, Ramadoss-C S, Ravindranath-B, Inhibition of Soybean Lipoxygenase-1 by Anacardic Acids, Cardols and Cardanols, Journal of Natural Products-Lloydia 1994, Vol 57, Iss 12, pp 1755-1757, Lee-J S Cho-Y S Park-F J Kim-J Oh-W K Lee-H S Ahn-J S, Phospholipase C-Gamma-1 Inhibitory Principles from the Sarcotestas of Ginkgo-Biloba, Journal of Natural Products 1998, Vol 61, Iss 7, pp 867-871, Synthesis of advanced materials including Liquid crystalline polymers were also reported from cardanol as exemplified in the following publications. Abraham-S Prasad-V S Pillai-C Ravindranathan-M, Copolyesters of Hydroxyphenylalkanoic Acids-Synthesis and Thermal-Properties of Poly ((4-Oxybenzoate)—Co—(8-(3-Oxyphenyl)Octanoate)) and Poly((3-Bromo-4-Oxybenzoate)—Co—(8-(3-Oxyphenyl) Octanoate)), Polymer International 2002, Vol 51, Iss 6, pp 475-480; Pillai-C K S Sherrington-D C Sneddon-A, Thermotropic Liquid-Crystalline Copolyester Based on 8-(3-Hydroxyphenyl) Octanoic-Acid and Para-Hydroxybenzoic Acid, Polymer 1992, Vol 33, Iss 18, pp 3968-3970; Saminathan-M Krishna-C Pillai-S Pavithran-C, Synthesis and Characterization of Main-Chain Liquid-Crystalline Polymers Containing a P-Phenyleneazo Group, Macromolecules 1993, Vol 26, Iss 25, pp 7103-7105; Liquid-Crystalline Polymers—The Effects of Chain Disrupters, Pure and Applied Chemistry 1998, Vol 70, Iss 6, pp 1249-1252, Saminathan-M Pillai-C K S, Synthesis of Novel Liquid-Crystalline Polymers with Cross-Linked Network Structures, Polymer 2000, Vol 41, Iss 8, pp 3103-3108, Synthesis of aryl acrylates based on cardanol were reported in the following publications. John-G Pillai-C K S, Synthesis and Characterization of a Self-Cross-Linkable Polymer from Cardanol—Autooxidation of Poly(Cardanyl Acrylate) to Cross-Linked Film, Journal of Polymer Science Part A-Polymer Chemistry 1993, Vol 31, Iss 4, pp 1069-1073, Nguyen-L H, Koerner-H Lederer-K, Cure Kinetics of the Cardanyl Acrylate-Styrene System Using Isothermal Differential Scanning Calorimetry, Journal of Applied Polymer Science 2002, Vol 85, Iss 9, pp 2034-2.

Flame retardant applications of Phosphorylated CNSL system were exemplified in the following publications. Prasad-V S Pillai-C K S, Flame Retardation of Polyethylene—Effect of a Phosphorus Flame-Retardant Having Both Hydrophobic and Hydrophilic Groups in the Same Molecule, Journal of Applied Polymer Science 2000, Vol 77, Iss 12, pp 2631-2640; Antony-R, Synthesis, Characterization, and Thermal Studies of Cardanol-Based Polyphosphate Esters, Journal of Polymer Science Part A-Polymer Chemistry 1993, Vol 31, Iss 13, pp 3187-3191, Pillai-C K S Prasad-V S Menon-A R R Sudha-J D Jayakumari-V G Kumar-M B Pavithran-C Tikku-V K Pradhan-N K, A Comparative-Evaluation of a Novel Flame-Retardant, 3-(Tetrabromopentadecyl)-2,4,6-Tribromophenol (TBPTP) with Decabromodiphenyloxide (DBDPO) for Applications in LDPE-Based and EVA-Based Cable Materials, Journal of Applied Polymer Science 1997, Vol 66, Iss 11, pp 2157-2173.

Polymerisation of modified cardanol and its applications were exemplified in the following publications. Manjula-S, Kumar-V G, Pillai-C K S, Kinetics and Mechanism of Oligomerization of Cardanol Using Acid Catalysts, Journal of Applied Polymer Science 1992, Vol 45, Iss 2, pp 309-315; Shobha-S V, Krishnaswamy-P R, Ravindranath-B, Antony-R, Pillai-C K S, Synthesis and Thermal Characterization of Chemically-Modified Cardanol Polymers, Journal of Applied Polymer Science 1993, Vol 49, Iss 12, pp 2129-2135; Agrawal-J P, Satpute-R S, Cardanol-Based Epoxy Flexibilizers for Inhibition of Composite Propellants, Journal of Macromolecular Science-Pure and Applied Chemistry 1993, Vol A30, Iss 1, pp 19-34, Swain-S K Sahoo-S Mohapatra-D K Mishra-B K Lenka-S Nayak-P L, Polymers from Renewable Resources-5. Synthesis and Characterization of Thermosetting Resins Derived from Cashew Nut Shell Liquid (CNSL)-Furfural-Substituted Aromatic-Compounds, Journal of Applied Polymer Science 1994, Vol 54, Iss 10, pp 1413-1421, Antony-R Pillai-C K S, Synthesis and Thermal Characterization of Chemically-Modified Phenolic Resins, Journal of Applied Polymer Science 1994, Vol 54, Iss 4, pp 429-438, Menon-A R R Pillai-C K S Nando-G B, Chemical Cross-Link Density and Network Structure of Natural-Rubber Vulcanizates Modified with Phosphorylated Cardanol Prepolymer, Journal of Applied Polymer Science 1994, Vol 51, Iss 13, pp 2157-2164, Sahoo-S K Swain-S K Mohapatra-D K Nayak-P L Lenka-S, Polymers from Renewable Resources-6: Synthesis and Characterization of Thermosetting Resins Derived from Cashewnut Shell Liquid Formaldehyde Substituted Aromatic-Compounds, Angewandte Makromolekulare Chemie 1995, Vol 233, Iss NOV, pp 1-13, Mishra-D K Parida-D Nayak-S S Lenka-S Nayak-P L, Polymers from Renewable Resources 0.10. Semiinterpenetrating Polymer Networks Based on Castor-Oil Polyurethane and Cardanol-Furfural Resin—Scanning Electron-Microscopy and XRD Studies, Journal of Macromolecular Science-Pure and Applied Chemistry 1995, Vol A32, Iss S4, Suppl 4, pp 499-510, Nayak-S S Mishra-D K Nayak-P L Lenka-S, Polymers from Renewable Resources 0.11. Synthesis and Characterization of Thermosetting Resins Derived from Cardanyl Acrylate Formaldehyde-Substituted Aromatic-Compounds, Journal of Macromolecular Science-Pure and Applied Chemistry 1995, Vol A32, Iss S4, Suppl 4, pp 511-521, Nair-CPR Bindu-R L Joseph-V C, Cyanate Esters Based on Cardanol Modified-Phenol-Formaldehyde Resins—Syntheses and Thermal-Characteristics, Journal of Polymer Science Part a-Polymer Chemistry 1995, Vol 33, Iss 4, pp 621-627, Tan-T T M, Cardanol-Lignin-Based Epoxy-Resins—Synthesis and Characterization, Journal of Polymer Materials 1996, Vol 13, Iss 3, pp 195-199, Tan-T T M, Cardanol-Lignin-Based Polyurethanes, Polymer International 1996, Vol 41, Iss 1, pp 13-16, Mishra-D K Mishra-B K Lenka-S Nayak-P L, Polymers from Renewable Resources 0.7. Thermal-Properties of the Semiinterpenetrating Polymer Networks Composed of Castor-Oil Polyurethanes and Cardanol-Furfural Resin, Polymer Engineering and Science 1996, Vol 36, Iss 8, pp 1047-1051.

Mohapatra-D K, Nayak-P L, Lenka-S, Polymers from Renewable Resources-21 Semiinterpenetrating Polymer Networks Based on Cardanol-Formaldehyde-Substituted Aromatic-Compounds Copolymerized Resins and Castor-Oil Polyurethanes—Synthesis, Structure, Scanning Electron-Microscopy and XRD, Journal of Polymer Science Part A-Polymer Chemistry 1997, Vol 35, Iss 15, pp 3117-3124, Cardanol-Phenol-Formaldehyde Resins—Thermal-Analysis and Characterization, Angewandte Makromolekulare Chemie 1996, Vol 243, Iss DEC, pp 77-85, Tan-T T M, Cardanol-Glycols and Cardanol-Glycol-Based Polyurethane Films, Journal of Applied Polymer Science 1997, Vol 65, Iss 3, pp 507-510, Thien-D T Vankhoi-N Khang-D Q Vanluyen-D, modification of rubber by cardanol-formaldehyde resins and epoxidized cardanol, journal of macromolecular science-pure and applied chemistry 1996, Vol A33, Iss 12, pp 1963-1972, Tan-T T M, Thermoplastic Composites Based on Jute Fiber Treated with Cardanol-Formaldehyde, Polymers & Polymer Composites 1997, Vol 5, Iss 4, pp 273-279, Das-T K Das-D Guru-B N Das-K N Lenka-S, Polymers from Renewable Resources—Xxviii—Synthesis, Characterization, and Thermal Studies of Semiinterpenetrating Polymer Networks Derived from Castor-Oil-Based Polyurethanes and Cardanol Derivatives Polymer-Plastics Technology and Engineering 1998, Vol 37, Iss 4, pp 427-435, Lin-J H Hu-B H, Study on the Cardanol-Aldehyde Condensation Polymer Containing Boron-Nitrogen Coordinate Bond, Chinese Journal of Polymer Science 1998, Vol 16, Iss 3, pp 219-225, Bhunia-H P Jana-R N Basak-A Lenka-S Nando-G B, Synthesis of Polyurethane from Cashew Nut Shell Liquid, a Renewable Resource, Journal of Polymer Science Part A-polymer Chemistry 1998, Vol 36, Iss 3, pp 391-400.

Nair-C P R Bindu-R L Ninan-K N, Recent Advances in Phenolic Resins, Metals Materials and Processes 1997, Vol 9, Iss 2, pp 179-200; Uyama-H Kohayashi-S: Enzymatic Polymerization Yields Useful Polyphenols, Chemtech 1999, Vol 29, Iss 10, pp 22-28, Bhunia-H P Nando-G B Basak-A Lenka-S Nayak-P L, Synthesis and Characterization of Polymers from Cashewnut Shell Liquid, a Renewable Resource III—Synthesis of a Polyether, European Polymer Journal 1999, Vol 35, Iss 9, pp 1713-1722, Bhunia-H P Nando-G B Chaki-T K Basak-A Lenka-S Nayak-P L, Synthesis and Characterization of Polymers from Cashewnut Shell Liquid, a Renewable Resource II—Synthesis of Polyurethanes, European Polymer Journal 1999, Vol 35, Iss 8, pp 1381-1391; Moreira-L F B Lucas-E F Gonzalez-G, Stabilization of Asphaltenes by Phenolic-Compounds Extracted from Cashew-Nut Shell Liquid, Journal of Applied Polymer Science 1999, Vol 73, Iss 1, pp 29-34, Guru-B N Das-T K Lenka-S,N, Polymers from Renewable Resources—Xxvii—Studies on Synthesis, Characterization, and Thermal-Properties of Resins Derived from Cardanyl Acrylate-Furfural-Organic Compounds, Polymer-Plastics Technology and Engineering 1999, Vol 38, Iss 1, pp 179-187, Swain-J R Biswal-S K Lenka-S, Polymer from Renewable Resources—Studies on Synthesis, Characterization, and Thermal-Properties of Resins Derived from Diazotized Cardanol-Formaldehyde-Organic Compounds, Polymer-Plastics Technology and Engineering 2000, Vol 39, Iss 5, pp 927-936, Bhunia-H P Basak-A Chaki-T K Nando-G B, Synthesis and Characterization of Polymers from Cashewnut Shell Liquid—A Renewable Resource V—Synthesis of Copolyester; European Polymer Journal 2000, Vol 36, Iss 6, pp 1157-1165, Mhaske-S B Bhingarkar-R V Sabne-M B Mercier-R Vernekar-S P, Synthesis and Characterization of End-Capped Polyimides and Their Gas-Permeability Properties; Journal of Applied Polymer Science 2000, Vol 77, Iss 3, pp 627-635, Ikeda-R Tanaka-H Uyama-H Kobayashi-S Enzymatic-Synthesis and Curing of Poly(Cardanol) Polymer Journal 2000, Vol 32, Iss 7, pp 589-593; Paul-R K Pillai-C K S, Melt/Solution Processable Conducting Polyaniline with Novel Sulfonic-Acid Dopants and Its Thermoplastic Blends, Synthetic Metals 2000, Vol 114, Iss 1, pp 27-35; Lubi-M C, Thachil-E T, Cashew Nut Shell Liquid—A Versatile Monomer for Polymer Synthesis, Designed Monomers and Polymers 2000, Vol 3, Iss 2, pp 123-153.

Coatings based on CNSL were exemplified in the following publications. Kobayashi-S Uyama-H Ikeda-R Artificial Urushi, Chemistry-A European Journal 2001, Vol 7, Iss 22, pp 4755-4760, Ikeda-R Tsujimoto-T Tanaka-H Oyabu-H Uyama-H Kobayashi-S Man-Made Urushi—Preparation of Cross-Linked Polymeric Films from Renewable Resources via Air-Oxidation Processes, Proceedings of the Japan Academy Series B-Physical and Biological Sciences 2000, Vol 76, Iss 10, pp 155-160.

Ikeda-R Tanka-H Uyama-H Kobayashi-S, Synthesis and Curing Behaviors of a Cross-Linkable Polymer from Cashew Nut Shell Liquid, Polymer 2002, Vol 43, Iss 12, pp 3475-3481; Pillot-J P Birot-M Dao-T M Vu-M D Hoang-N L T Tran-T S, The Use of Naturally-Occurring Phenols in the Synthesis of Novel Functional Polysiloxanes, Surface Coatings International Part B-Coatings Transactions 2001, Vol 84, Iss 3, pp 197-204. There is no reported literature on the highly hydroxylated cardanol derivatives.

It is important to explore and review the use of renewable resource based FR additives for plastics which may be cost effective. Pillai et al. and Prasad et al. reported on synthesis of novel phosphorus FRs, and properties of monophosphorylated product of cardanol which is a renewable resource and a byproduct of cashew industry. They have shown that the phosphorylated CNSL is an effective non-halogen polymeric flame retardant for plastics and elastomers which will not leech out or bloom from the products. The phosphorus content in PCNSL is only 7.9%. It is known that with the increase in P content the flammability can be better. Cardanol can be further functionalized by hydroxylation and phosphorylated for getting higher P content to be a more effective flame retardant. A series of polyphosphates were prepared from derivatives of cardanol-phosphorodichloridates and dihydric phenols such as hydroquinone, bisphenol, tetrabromobisphenol and phenolphthalein by interfacial polycondensation (S. Zhang, A. R. Horrocks, Prog. Polym. Sci. 28, 11, 2003, 1517-1538).

There is a strong demand for non-halogen flame retardants for plastics especially in the consumer and construction fields due to safety concerns associated with higher toxic fumes and related casualties in the case of fire associated with plastic building materials with brominated flame retardants. In this context inorganic fillers like hydrated alumina, talc etc. are effective but at the cost of mechanical properties of the product.

Most acrylates disclosed in the prior art contain one or two acrylate groups per molecule. However, to achieve fast cure and high crosslinking density it is desirable that multifunctional cross-linkers having at least 3 functional groups per molecule are added to the formulations. Multifunctional hydrocarbon monomers such as acrylates, vinyl ethers and epoxies have been widely used as cross-linkers but their poor solubility and low boiling point limits their applications in low volatile organic coatings. High shrinkage is another disadvantage of aliphatic acrylate based coatings compared to aliphatic commercial acrylates. Ausimont USA of Thorofare N.J. provides Fluorolink T and T10, which have four hydroxyl groups per molecule. It is well known to those skilled in the art, due to steric hindrance, it is very difficult to fully convert the secondary hydroxyl groups to other functional groups such as acrylates, epoxies, and vinyl ethers, especially in the presence of primary hydroxyl groups. Incomplete conversion of hydroxyl groups makes it less suitable for applications requiring low moisture uptake and low optical absorption in the 1300-1600 nm wavelength regions.

U.S. Pat. No. 6,229,054 of Cardolite Corporation are on the preparation of derivatives of cardanol and CNSL and U.S. Pat. No. 6,451,957 deals with the process for the preparation of 8-(3-hydroxyphenyl)octanol from cardanol.

It is well known in the art that actinic radiation such as UV light permits fast curing. UV curable compositions containing multifunctional acrylates, oligomers and polymers have been widely reported. See, for example, Chem. Eng. News 2001, Nov. 5, K. D. Weiss, Prog. Polym. Sci. Vol. 22, 203-245, 1997. U.S. Pat. Nos. 4,508,916; 4,511,209; 4,914,171; 5,024,507; 5,062,680; 5,223,593; 5,822,489; 6,133,472; European patent No. 333,464A1; and publications including J. Pacansky, Progress in Organic Coatings, 18, 1990, 79 and R. Bongiovanni, Progress in Organic Coatings, 36 (1999) 70; all of which are herein incorporated by reference. These compositions comprise fluorinated mono- or multi-functional acrylates or vinyl ethers and at least one photo initiator.

It is well known that Phosphates are used as non-halogen flame retardants especially in plastics which will act in the condensed phase as well as in the vapour phase for effective flame retardation. See for example U.S. Pat. Nos. 6,569,928, 3,697,499, 4,010,144, 4,070,336, 4,073,767, 4,105,825, 4,073,829, 6,630,565, 5,650,531, 6,733,698 and publications including S. Zhang, A. R. Horrocks, Prog. Polym. Sci. 28, 11, 2003, 1517-1538, S-Y Lu, I. Hamerton Prog. Polym. Sci. 27, 2002, 1661-1712. U.S. Pat. No. 6,569,928 comprise phosphorylated flame retardants used in plastics. New methodologies for the Phosphorylation of alcohols including phenols were reported in J. K. Stowell, T. S. Widlanski, Tetrahedron Lett. 36, 11, 1995, 1825-1826.

Therefore there is no reported literature on the derivatisation of cardanol or Cashew nut shell liquid to a multifunctional alcohol which are more cost effective, having higher boiling and thermal properties and having at least 3 and upto 6 alcohol groups per molecule on their mixture.

OBJECTS OF THE INVENTION

The main object of the invention is to provide a process for the preparation of highly hydroxylated cardanol derivative with atleast 3 hydroxyl groups including atleast two hydroxyl groups in the side chain which can be used in the preparation of polyurethanes, polycarbonates epoxies etc.

Another object of the invention is to provide a process for the preparation of a multifunctional alcohol or polyol from cardanol which is soluble in polar solvents including water.

It is a further object of the invention to provide a process for the preparation of a multi functional acrylate from the said derivative which can be used as a renewable resource based low cost low boiling cross-linker in UV curable or photo curable other acrylic coating formulations including low volatile organic content coatings.

Another object of the invention is to provide a process for the preparation of highly pendent phosphorous containing cardanol derivative with atleast three phosphorus atoms per molecule which can be used as a phosphorus additive in flame retardant formulations.

A further object of the invention is to provide a process for the preparation of an amphiphilic surfactant molecule from cardanol.

Yet another object of the invention is to provide a process for the preparation of a multifunctional acrylate which will cure >125 seconds under Ultra Violet (UV)-radiation.

A further object of the invention is to provide a process for the preparation of a multifunctional phosphate flame retardant on curing with aldehydes will show a limiting oxygen index (LOI) value >35.

SUMMARY OF THE INVENTION

The present invention relates to the synthesis of a multifunctional acrylate or methacrylate containing aryl group as a multifunctional crosslinking agent for acrylic polymers especially paints and coatings.

The present invention also relates to the synthesis of a non-halogen flame retardant monomer or oligomer containing highly pendant phosphorus moieties. In particular, it relates to a process for preparing the flame retardant phosphorus-containing compound through an esterification reaction.

Multifunctional alcohols and their acrylate and phosphate derivatives prepared by the process of the present invention have the structure given below.

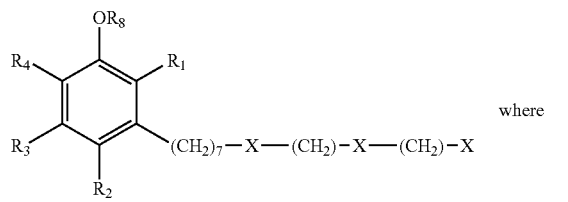

where

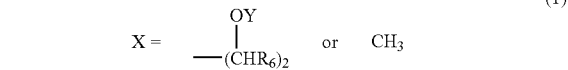

(1)

(2)

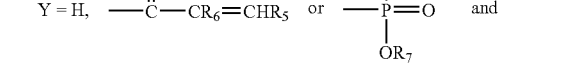

and (3)

$R_1$ = H, OH, COOH, or alkyl
$R_2$ = H, OH, COOH or Halogen
$R_3$ = H, OH, alkyl, aryl, alkoxy or aryloxy or halogen
$R_4$ = H, OH, COOH, alkyl, aryl or halogen
$R_5$ = H, alkyl, alkyl ester, aryl or halogen
$R_6$ = H, OH, alkyl, aryl or halogen
$R_7$ = H, OH, halogen, alkoxy, aryloxy, aryl or alkyl ester
$R_8$ = H, alkyloyl, aryloyl or Y Accordingly, the present invention provides a process for the preparation of multifunctional alcohols or its acrylates or phosphates derived from cashew nut shell liquid, cardanol or its components of the general formula given above, comprising of the steps of acetylation of cardanol using acetic anhydride in presence of catalysts such as p-toluene sulphonic acid, benzene sulphonic acid and sulphuric acid at temperature in the range of 30-80° C. for 2-4 h.

In another embodiment of the finding the solvent used for acetylation of cardanol is selected from N,N-dimethyl formamide, dimethyl sulphoxide, methanol, tetrahydrofuran and acetone.

In another embodiment of the present invention, the acid anhydride used in the acetyaltion step is selected from the group consisting of phthalic anhydride, trifluoroacetic anhydride, acetic anhydride and chloroacetic anhydride.

In a further embodiment of the invention, the metal oxide used in the step of transhydroxylation is selected from the group comprising of, Magnesium Oxide, Nickel oxide, Tungsten oxide, Rhenium Trioxide and Titanium oxide.

In another embodiment of the present invention, the temperature used for transhydroxylation ranges between 50-140° C.

In another embodiment of the present invention, the time of transhydroxylation ranges between 2-12 hrs.

In another embodiment of the finding the acryloylation or methacryloylation of the hydroxylated derivative of cardanol or CNSL is carried out in presence of acryloyl chloride, methacryloyl chloride and 2-ethylhexylacryloyl chloride.

In another embodiment of the finding the temperature of acryloylation is 30-45° C.

In another embodiment of the finding the catalyst used in acryloylation is amines selected from methyl amine, triethyl amine, trimethyl amine and diethylamine.

In another embodiment of the finding, phosphorylation of the hydroxylated cardanol was carried out using phosphorylating agents selected from phosphorus pentoxide, phosphoric acid, phosphorodichloridate and diethyl phosphite.

In another embodiment of the present invention, the acrylate has cured within 120 seconds under UV lamp.

In another embodiment of the present invention, the phosphate derivative shows a Limiting Oxygen Index value above 35.

The main finding underlying the present invention is our observation that a process for the preparation of hydroxylated cardanol and its derivatives where one of the hydroxylated products is water soluble with hydroxyl value of >1500 mg of KOH. The acryloylated derivative showed complete curing under UV lamp below 120 seconds under a mylar sheet. The phosphorylated derivative of the above showed a Limiting Oxygen Index of >35 under ASTM D2863-76 test conditions and a V-0 rating under UL-94 flame tests.

DETAILED DESCRIPTION OF THE INVENTION

The process of the present invention has essentially the following steps: acetylation of cardanol or CNSL in presence of excess acid anhydrides selected from propionic anhydride, acetic anhydride and trifluoroacetic anhydride: and trans-hydroxylation of the acyloxy derivative in presence of hydrogen peroxide or Sodium perborate in presence of acids selected from acetic acid, formic acid, peracetic acid and performic acid and metal oxides selected from the group comprising of transition metal oxides or Magnesium Oxide, Nickel oxide, Tungsten oxide, Rhenium Trioxide and Titanium oxide at temperatures of 50-140° C. for 2-6 hrs. This was optionally followed by hydrolysis using alkali solution and a purification step involving extraction using solvent mixtures selected from acetone-methanol, acetone-methyl ethyl ketone and acetone-isopropanol mixture and drying under reduced pressure at 30-60° C. for 1-4 h.

The acryloyl derivative was prepared by acylation using acid chloride at ice bath conditions in presence of amines as catalysts, the acryloylation or methacryloylation of the hydroxylated derivative of cardanol or CNSL is carried out in presence of acryloyl chloride, methacryloyl chloride and 2-ethylhexylacryloyl chloride at a temperature of −5 to 45° C. in presence of amines selected from methyl amine, triethyl amine, trimethyl amine and diethylamine for a time varies from 1-3 h.

The phosphorylated derivative of the hydroxylated cardanol was carried out using phosphorylating agents selected from phosphorus pentoxide, phosphoric acid, phosphorodichloridate and diethyl phosphate at a temperature of 50-120° C. using solvents selected from N,N-dimethyl formamide, dimethyl sulphoxide, methanol, tetrahydrofuran and acetone for a time of 2-6 h. The purification of the product was done by solvent extraction using solvents or mixture of solvents selected from N,N-dimethyl formamide, dimethyl sulphoxide, methanol, tetrahydrofuran, water and acetone and drying under reduced pressure at 30-60° C. for 1-4 h.

The main finding underlying the present invention is our observation that a process for the preparation of hydroxylated cardanol and its derivatives where one of the hydroxylated products is water soluble with hydroxyl value of >1500 mg of KOH. The acryloylated derivative showed complete curing under UV lamp below 120 seconds under a mylar sheet. The phosphorylated derivative of the above showed a Limiting Oxygen Index of >35 under ASTM D2863-76 test conditions and a V-0 rating under UL-94 flame tests.

The invention is described in detail in the following examples, which are provided by way of illustration only and should not be construed to limit the scope of the invention.

EXAMPLE 1

Synthesis of 1-acetoxy-3-(8,11,14-pentadecatrienyl) benzene: A mixture of acetic anhydride (0.1 mol, 15 ml) and p-toluenesulphonic acid (PTSA, 3.15 mol %, 0.6 g) were taken in a two necked RB flask and double distilled cardanol (0.1 mol, 30 g) was added dropwise with stirring over a period of 30 minutes at ambient conditions. The reaction was continued for 8-12 h. The product (AC) was washed free of acetic acid and catalyst with water and dried.

EXAMPLE 2

Hydroxylation using peroxide with metal oxide: A mixture of 50% $H_2O_2$ (0.66 mol, 26.5 ml), MgO (0.4 mol %, 0.1 g) and $CH_3COOH$ (25 ml, solvent) were taken in a RB flask fitted with reflux condenser and heated to 50-70° C. The product obtained from Example 1 was added drop wise over a period of 1 hr. It was kept over night under stirring at ambient conditions. Metal oxide was filtered off and the mixture was washed with excess of water. It was hydrolysed by 10% NaOH solution and neutralized by dil. HCl, followed by washing with water and dried as mentioned in example 1. The yield of the product (HC) obtained was 95%.

EXAMPLE 3

A mixture of 50% $H_2O_2$ (10.2 ml, 0.15 mol) and 85% formic acid (8.12 ml, 0.15 mol) was taken in 100 ml RB flask and acetylated cardanol (0.15 mole) was added drop wise with constant stirring in ice-cold. It was hyrolysed by dil. NaOH solution and neutralized by dil. HCl. Then it was washed with water and dried as mentioned earlier. The yield obtained was 95%.

EXAMPLE 4

Synthesis of Phosphorylated Derivative: HC (0.1 mol) and DMF (25 ml) were taken in a two-necked RB flask connected with reflux condenser and stirred using magnetic stirrer. To the stirring solution, $P_2O_5$ (0.022 mol, 3.19 g) was added portion wise. It was heated to 60-70° C. for 6 hrs. The solvent was removed and it was washed with water. Then it was dried in an air oven at 60° C. under reduced pressure. (Yield 84%).

EXAMPLE 5

Synthesis of Phosphorylated Derivative: A mixture of anhydrous $AlCl_3$ (0.001 mol %) and $POCl_3$ (0.06 mol, 5.68 ml) in DMF (10 ml) was taken in a two necked RB fitted with a reflux condenser and heated to reflux. HC (0.0067 mol, 2 g) in DMF was added drop wise with stirring over a period of 30 minutes. $AlCl_3$ was filtered off and the solvent was separated. It was precipitated in acetone.

EXAMPLE 6

Synthesis of Phosphorylated Derivative: $I_2$ (3.19 g, 0.025 mol) was added to a solution of diethyl phosphite (2.68 ml, 0.02 mol) in ethyl acetate (5 ml) at 0° C. After 5 min. the clear, solution was allowed to warm to 25° C. The above solution was added dropwise over a period of 10-15 mts, to a flask containing HC (1 g, 0.0025 mol) and pyridine (2 ml) in ethyl acetate (5 ml) at 0° C. After 10 min. it was washed with aqueous $NaHSO_4$ Solvent was removed and the product was dried. Yield was 60%.

EXAMPLE 7

Phosphorylation using Orthophosphoric acid: 85% ortho phosphoric acid (6 ml) in ethyl acetate was taken in a RB flask and HC (5 g, 0.012 mol) in ethyl acetate was added drop wise. It was heated to 160° C. for 2 hrs with stirring.

EXAMPLE 8

Acryloylated Derivative of HC: 1.5 g of HC (0.0023 mol was taken in a 100 ml R.B. flask. 2.15 g of triethyl amine (0.96 mol) in 1:6 ratio and about 5 ml of toluene as solvent were added. In a pressure equalizing funnel, 2.2 g of acryloyl chloride was added in 1:7 ratio (0.012 moles) in 5 ml toluene as solvent. Then acryloyl chloride is added dropwise to allow a controlled reaction. The reaction was kept in an ice bath to control the vigorous reaction. Then the reaction was continued for 5 hrs. Separated and Purified by column.

EXAMPLE 9

Methacryloylated Derivative of HC:1.5 g of HC (0.0023 mol was taken in a 100 ml R.B. flask. 2.15 g of triethyl amine (0.96 mol) in 1:6 ratio and about 5 ml of toluene as solvent were added. In a pressure equalizing funnel, 2.2 g of methacryloyl chloride was added in 1:7 ratio (0.012 moles) in 5 ml toluene as solvent. The reaction was kept in an ice bath to control the vigorous reaction. Then the reaction was continued for 5 hrs. Separated and Purified by column.

The advantages of the present invention are the following:

The present invention provides a process for the preparation of hydroxylated cardanol. The acryloylated derivative showed complete curing under UV lamp within 60-120 seconds under a mylar sheet. The phosphorylated derivative of the above showed a Limiting Oxygen Index of 40 under ASTM D2863-76 testing and a V-0 rating under UL-94 flame tests.

We claim:

1. A multifunctional alcohol, or acrylate or phosphate derivative thereof, having a structure:

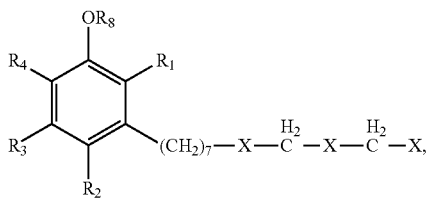

wherein:
$X$=each independently $—(C(OY)R_6)—(CH(OY)R_6)$ at terminal position and $—(C(OY)R_6)_2—$ at linking position
$Y$=each independently H, $—C(O)—CR_6=CHR_5$ or $—P(OR_7)_2O$
$R_1$=H, OH, COOH or alkyl
$R_2$=H, OH, COOH or Halogen
$R_3$=H, OH, alkyl, aryl, alkoxy, aryloxy or halogen
$R_4$=H, OH, COOH, alkyl, aryl, or halogen
$R_5$=each independently H, alkyl, alkyl ester, aryl or halogen
$R_6$=each independently OH, alkyl, aryl or halogen
$R_7$=each independently H, OH, halogen, alkoxy, aryloxy, aryl or alkyl ester
$R_8$=H, alkyloyl, aryloyl or Y
wherein the compound comprises at least three hydroxyl groups including at least two in the side chain.

2. A process for the preparation of multifunctional alcohol from cardanol, or an acryloylated derivative or phosphorylated derivative thereof, comprising the steps of:
acetylating cardanol or a derivative thereof,
followed by transhydroxylation of the resulting product,
to obtain a multifunctional alcohol, or an acryloylated or phosphorylated derivative thereof, having a formula:

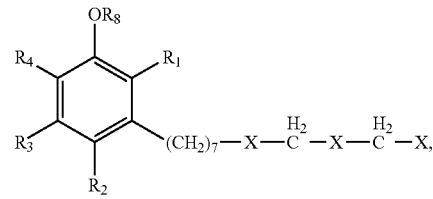

wherein:
$X$=each independently $—(C(OY)R_6)—(CH(OY)R_6)$ at terminal position and $—(C(OY)R_6)_2—$ at linking position
$Y$=each independently H, $—C(O)—CR_6=CHR_5$ or $—P(OR_7)_2O$
$R_1$=H, OH, COOH or alkyl
$R_2$=H, OH, COOH or Halogen
$R_3$=H, OH, alkyl, aryl, alkoxy, aryloxy or halogen
$R_4$=H, OH, COOH, alkyl, aryl or halogen
$R_5$=each independently H, alkyl, alkyl ester, aryl or halogen
$R_6$=each independently OH, alkyl, aryl or halogen
$R_7$=each independently H, OH, halogen, alkoxy, aryloxy, aryl or alkyl ester
$R_8$=H, alkyloyl, aryloyl or Y
wherein the compound comprises at least three hydroxyl groups including at least two in the side chain.

3. The process of claim 2 wherein acetylation is carried out using an acid anhydride selected from the group consisting of phthalic anhydride, chloroacetic anhydride, propionic anhydride, acetic anhydride and trifluoroacetic anhydride.

4. The process of claim 2 wherein acetylation is carried out in the presence of a solvent selected from the group consisting of N,N-dimethylformamide, dimethylsulphoxide, methanol and tetrahydrofuran.

5. The process of claim 2 wherein acetylation is carried out using a catalyst selected from the group consisting of p-toluene sulphonic acid, benzene sulphonic acid and sulphuric acid.

6. The process of claim 2 wherein hydroxylation is carried out in the presence of a reagent selected from the group consisting of hydrogen peroxide, Sodium perborate, Formic acid, peracetic acid, performic acid or a metal oxide selected from the group consisting of a transition metal oxide, Tungsten oxide, Magnesium Oxide and Nickel oxide.

7. The process of claim 2 wherein the temperature used for the transhydroxylation is between 30-120° C.

8. The process of claim 2 wherein the time of transhydroxylation ranges between 2-12 hrs.

9. The process of claim 2 wherein the hydroxylated cardanol is highly water soluble with hydroxyl value of >1500 mg of KOH.

10. The process of claim 2 wherein phosphorylation of the hydroxylated cardanol is carried out using a reagent selected from the group consisting of phosphorus pentoxide, phosphoric acid, phosphoro dichloridate and diethyl phosphite.

11. The process of claim 2 wherein acryloylation or methacryloylation is carried out in presence of acryloyl chloride or methacryloyl chloride in the presence of a triethyl amine catalyst or a base at a temperature in the range of 0-50° C.

12. The process of claim 2 further comprising a step where the acrylate is cured within 120 seconds under UV lamp under a Mylar sheet.

13. The process of claim 2 wherein the phosphorylated derivative has a Limiting Oxygen Index of >35 under ASTM D2863-76 testing and a V-0 rating under UL-94 flammability tests.

* * * * *

UNITED STATES PATENT AND TRADEMARK OFFICE
CERTIFICATE OF CORRECTION

| | |
|---|---|
| PATENT NO. | : 8,378,135 B2 |
| APPLICATION NO. | : 12/097354 |
| DATED | : February 19, 2013 |
| INVENTOR(S) | : Vadekkethonippurathu Sivankutty Nair Prasad et al. |

It is certified that error appears in the above-identified patent and that said Letters Patent is hereby corrected as shown below:

On the Title page, item (57) Abstract, line 5, delete ">phosphates" and insert --phosphates-- therefor.

Signed and Sealed this
Nineteenth Day of March, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,378,135 B2
APPLICATION NO. : 12/097354
DATED : February 19, 2013
INVENTOR(S) : Prasad et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1107 days.

Signed and Sealed this
Eleventh Day of November, 2014

Michelle K. Lee
*Deputy Director of the United States Patent and Trademark Office*